United States Patent
Wu et al.

(10) Patent No.: US 9,480,439 B2
(45) Date of Patent: Nov. 1, 2016

(54) SEGMENTATION AND FRACTURE DETECTION IN CT IMAGES

(71) Applicant: Virginia Commonweath University, Richmond, VA (US)

(72) Inventors: Jie Wu, Richmond, VA (US); Rosalyn Hobson Hargraves, Richmond, VA (US); Kayvan Najarian, Richmond, VA (US); Ashwin Belle, Richmond, VA (US); Kevin R. Ward, An Arbor, MI (US)

(73) Assignee: Virginia Commonwealth University, Richmond, VA (US)

( * ) Notice: Subject to any disclaimer, the term of this patent is extended or adjusted under 35 U.S.C. 154(b) by 131 days.

(21) Appl. No.: 14/070,457

(22) Filed: Nov. 1, 2013

(65) Prior Publication Data
US 2014/0233820 A1   Aug. 21, 2014

Related U.S. Application Data

(60) Provisional application No. 61/721,061, filed on Nov. 1, 2012.

(51) Int. Cl.
| | |
|---|---|
| *G06K 9/00* | (2006.01) |
| *A61B 6/03* | (2006.01) |
| *A61B 6/00* | (2006.01) |
| *G06T 7/00* | (2006.01) |
| *G06K 9/62* | (2006.01) |

(52) U.S. Cl.
CPC ............ *A61B 6/032* (2013.01); *A61B 6/505* (2013.01); *A61B 6/5211* (2013.01); *G06K 9/6204* (2013.01); *G06T 7/0014* (2013.01); *G06T 2200/04* (2013.01); *G06T 2207/10081* (2013.01); *G06T 2207/30008* (2013.01)

(58) Field of Classification Search
None
See application file for complete search history.

(56) References Cited

U.S. PATENT DOCUMENTS

| | | | |
|---|---|---|---|
| 8,229,222 B1* | 7/2012 | Silver | G06K 9/00 382/181 |
| 2006/0094951 A1* | 5/2006 | Dean et al. | 600/407 |
| 2011/0036360 A1* | 2/2011 | Lang et al. | 128/898 |
| 2012/0143037 A1* | 6/2012 | Najarian et al. | 600/407 |

FOREIGN PATENT DOCUMENTS

WO   WO 2010117575 A2 * 10/2010

OTHER PUBLICATIONS

Cootes et al., Active shape models—Their training and application, Computer Vision and Image Understanding, 61(1):38-59 (1995).
Wu et al., A New Hierarchical Method for Multi-level Segmentation of Bone in Pelvic CT Scans, IEEE Engineering in Medicine and Biology Society, pp. 3399-3402 (2011).
Wu et al., Fracture detection in traumatic pelvic CT images, Int. J. Biomed. Imaging, vol. 2012, Article ID 327198, 10 pages (2012).

* cited by examiner

*Primary Examiner* — Weiwen Yang
(74) *Attorney, Agent, or Firm* — Marshall, Gerstein & Borun LLP

(57) ABSTRACT

Provided is a new hierarchical methodology having a series of computational steps such as adaptive window creation, 2-D SWT application, masking, and boundary tracing is proposed. The techniques and systems are able to detect and quantify fracture as well as to generate recommendations for decision-making and treatment planning in traumatic pelvic injuries.

22 Claims, 18 Drawing Sheets

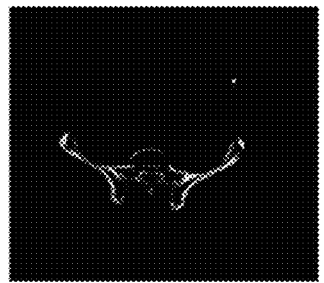 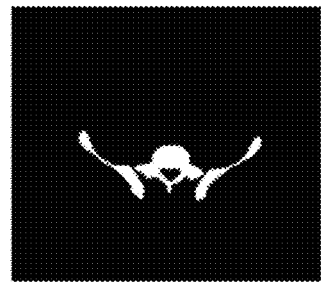 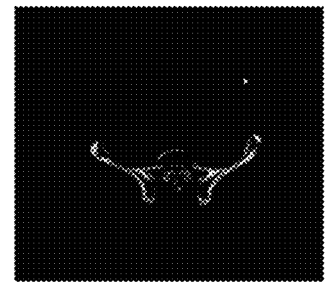
*FIG. 7a*  *FIG. 7b*  *FIG. 7c*
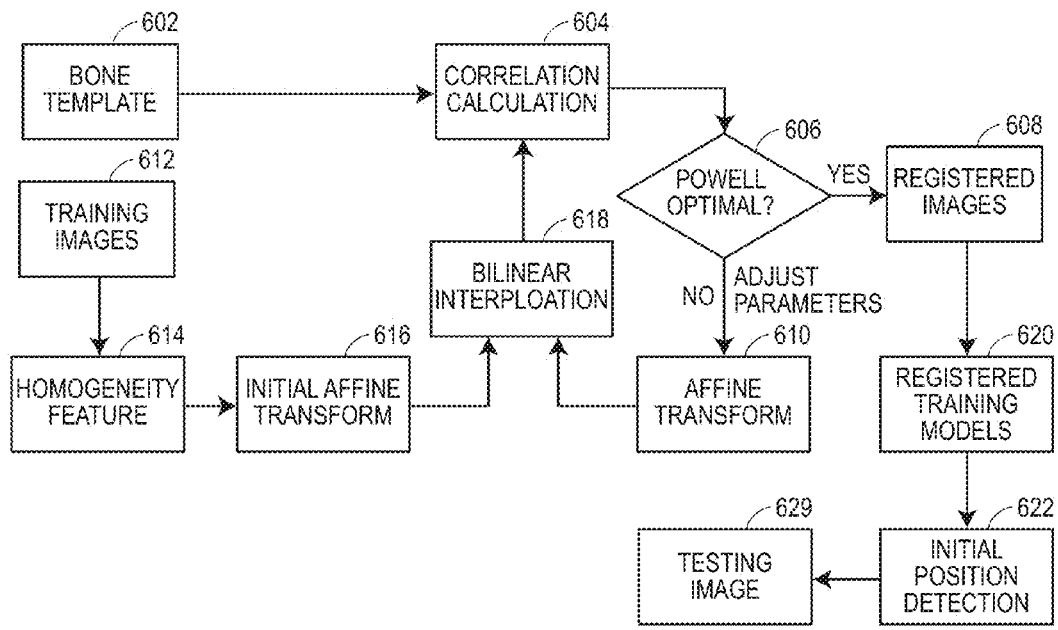
*FIG. 8*

SEGMENTATION AND FRACTURE DETECTION IN CT IMAGES

CROSS-REFERENCE TO RELATED APPLICATION

This application claims the benefit of U.S. Application No. 61/721,061, filed Nov. 1, 2012, entitled "Segmentation and Fracture Detection in CT Images for Traumatic Pelvic Injuries," which is hereby incorporated by reference in its entirety.

BACKGROUND

Medical data contains information that is vital for clinical diagnosis as well as treatment planning. Nowadays, varieties of clinical data are not optimally and comprehensively utilized towards medical decision making. This is because simple human inspection or traditional computational methods are incapable of extracting the hidden patterns contained in the data, which are very important to form recommendations and predictions for both diagnosis and treatment planning. In recent decades, more types and quantities of medical data have been collected due to advanced technology. A large number of significant and critical information is contained in these medical data. Still, highly-efficient, automated computational methods are needed to process and analyze the available medical data, in order to provide the physicians with recommendations and predictions on diagnostic decisions and treatment planning.

Traumatic pelvic injury is a severe yet common injury in the United States, often caused by motor vehicle accidents or fall. Commonly, pelvic injuries are assessed using information contained in the pelvic Computed Tomography (CT) images, making these images important for assessing the severity and prognosis of traumatic pelvic injuries. Each pelvic CT scan includes a large number of slices. Meanwhile, each slice contains a large quantity of data that may not be thoroughly and accurately analyzed via simple visual inspection with the desired accuracy and speed. Hence, a computer-assisted pelvic trauma decision-making system would be valuable to assist physicians in making accurate diagnostic decisions and determining treatment planning in a short period of time. Currently, however, due to factors such as limited resolution of medical images, variations in bone tissues, complexity of pelvic structures, and significantly different geometrical characteristics of fractures, automatic detection and segmentation of pelvic bone and, more valuably, detection of the bone fractures using CT scan imaging remains a significant challenge. Moreover, the existing decision-making systems for such traumatic injuries do not extract and/or consider the features automatically detected from medical images.

BRIEF DESCRIPTION OF THE DRAWINGS

FIGS. 7(a)-7(c) are CT pelvic images of a homogeneity features based image registration, in accordance with an example.

FIG. 8 is a flow diagram of a process for implementing a registered Active Shape Model process (RASM), in accordance with an example.

DETAILED DESCRIPTION

Pelvic bone segmentation is a useful step in analyzing pelvic CT images and assisting physicians with diagnostic decisions in traumatic pelvic injuries. The present techniques provided a new hierarchical segmentation approach capable of automatically extracting multiple-level bone structures using a combination of anatomical knowledge and computational techniques. For example, first, morphological operations, image enhancement, and edge detection may be performed for preliminary bone segmentation. The proposed techniques then may use a template-based best-shape matching method that provides an entirely automated segmentation process. This may be followed by a what is called herein a Registered Active Shape Model (RASM) process that extracts pelvic bone tissues using more robust training models than standard ASM models. In addition, a hierarchical initialization process may be used for the RASM in order to address the shortcoming of the standard ASM, in particular the high sensitivity to initialization endemic to conventional systems.

In an example, two suitable measures may be defined to evaluate the segmentation results: 1) mean distance and 2) mis-segmented area to quantify the segmentation accuracy. Successful segmentation results indicate effectiveness and robustness of the proposed algorithm. The techniques allow for building three-dimensional (3D) pelvic bone models, which were built, as discussed, after pelvic bone structures were segmented using consecutive 2D CT slices.

The techniques herein, providing automatic and accurate detection of the fractures from segmented bones in traumatic pelvic injuries, can help physicians detect the severity of injuries in patients. The extraction of fracture features (such as presence and location of fractures) as well as fracture displacement measurement are useful for assisting physicians in making faster and more accurate decisions. Thus with the present techniques, after bone segmentation, fracture detection may be automatically performed using a hierarchical approach based on wavelet transformation, adaptive windowing, boundary tracing and masking. Also, a quantitative measure of fracture severity based on pelvic CT scans may be defined. The results demonstrate that techniques are not only capable of automatically detecting both major and minor fractures, but can also be used for clinical applications.

Figure 1:
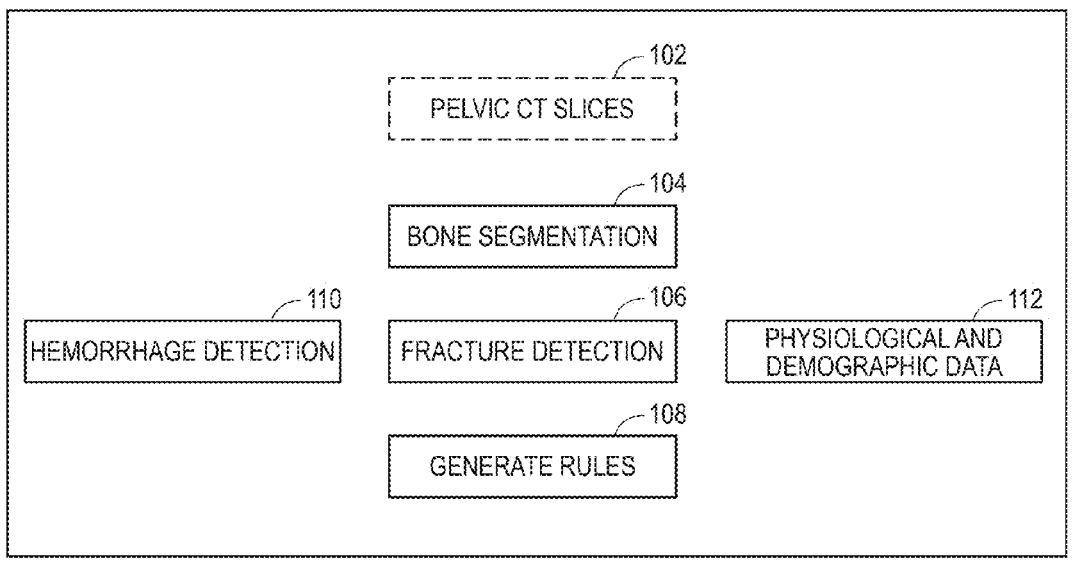
FIG. 1 is a block diagram of a schematic diagram of an example of decision support system, in accordance with an example.

FIG. 1 illustrates a schematic diagram of an example of decision support system 100, as may be implemented in a computer system such as that of FIG. 19, described below. In this example, CT slides (image slices) are provided and stored in a memory 102. The system 100 further includes a bone segmentation module 104, a fracture detection module 106, a rules generation module 108, and a hemorrhage detection module 110, each able to access physiological and demographic data 112 stored in the system 100, or stored for access by the system 100, as would be the case for the image data 102, as well.

Figure 2:
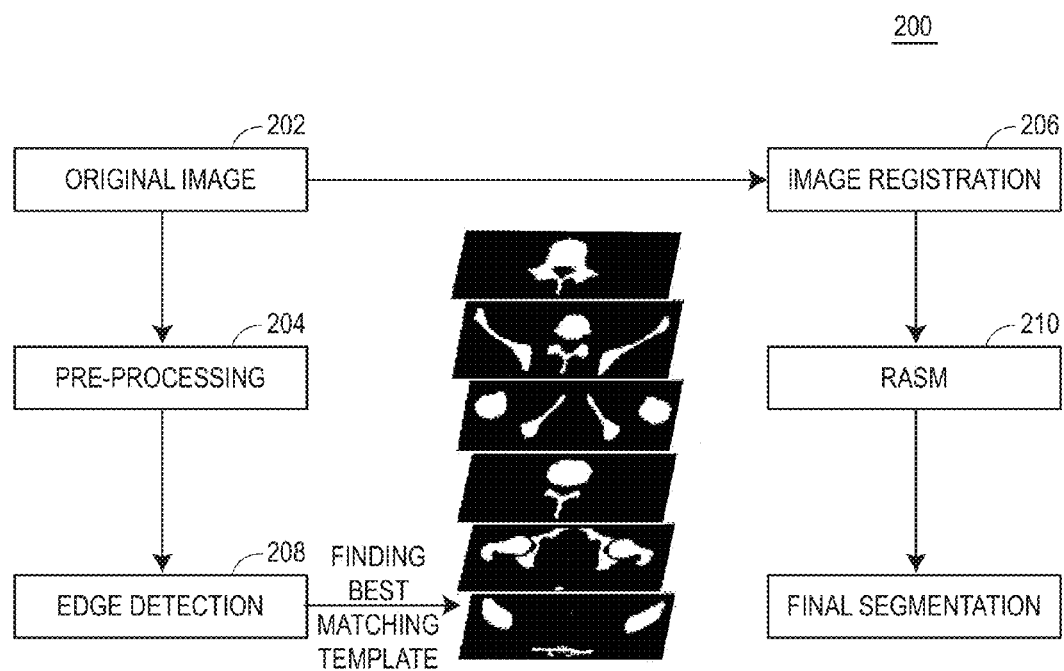
FIG. 2 is a flow diagram a segmentation process, as may be performed with the system of FIG. 1, in accordance with an example.

FIG. 2 is a flow diagram a segmentation process 200 as may be implemented by the system 100. Initially, the original CT image data is obtained at a block 202 and provided to a pre-processing block 204 and an image registration block 206, both of which will be described in more detail below.

Pre-Processing

The pre-processing block 204, in this example, separates initial image objects that are not part of the target image as well as enhancing the quality of the image by removing the noise while maintaining the bone edges. There exist different surrounding artifacts in the original image, e.g. CT table, cables, hands, and lower extremities. The block 204 may separate from the received images those artifacts or other pre-determined elements, including body parts like the abdomen from the original pelvic CT image data. Morphological operations may be performed on this image data to separate different regions and to select the region with the largest area. A median filter may be applied to remove high frequency speckle noise without compromising the edges.

An example extraction of the abdomen image parts, as performed by the block 204, would be as follows. First, in order to extract the abdominal region, a binary image is created based on the original CT image. A specified intensity value is set as the threshold. The pixels whose intensity values are higher than this threshold are set to 1, and the pixels whose intensity values are less or equal to this threshold are set to 0. The abdominal region and some of the surrounding artifacts have a higher gray level value than the background. Consequently, the abdominal region and some of the artifacts are well separated from the background.

Second, morphological operations are conducted on the binary image. This step is designed to separate different objects in the extracted image. The pelvic region and some artifacts may be connected together in the extracted image, for example; and morphological operations are applied to make them disconnected and separated.

Third, the region with the largest area, e.g., the abdomen, is then selected. In this step, first the features of different regions, such as the area and centroid are calculated. Then, the region with the largest area is separated and selected.

Fourth, a mask is created with the same size of the identified region in preceding step. This allows additional artifacts to be removed.

Fifth, after the abdomen region is selected, a median filter is applied in order to remove the existing high frequency speckle noise in the image. This step helps reduce or eliminate noise, as the noise can affect features of the structures of interest and degrade the overall quality of the image. Median filters are described using a mask in space. Median filters reduce noise without destroying the edges. By using a median filter, the grey-level of each pixel is replaced by the median of the grey levels in the mask. What makes median filters differ from lowpass linear filters is the use of "median" as opposed to "average". Each of the original images is then processed based on the example steps above.

Image Enhancement

In some examples, image enhancement techniques are applied further applied as part of the image pre-processing of block 204.

Image enhancement may be used to improve the interpretability or perception of information in images for viewers. Image enhancement is involved in our algorithm to emphasize the features of interest, the pelvic region, while simultaneously put less emphasis on soft tissues and other organs. This ensures that the original image quality is improved with "better" information reflected about pelvic bones.

Figure 3:
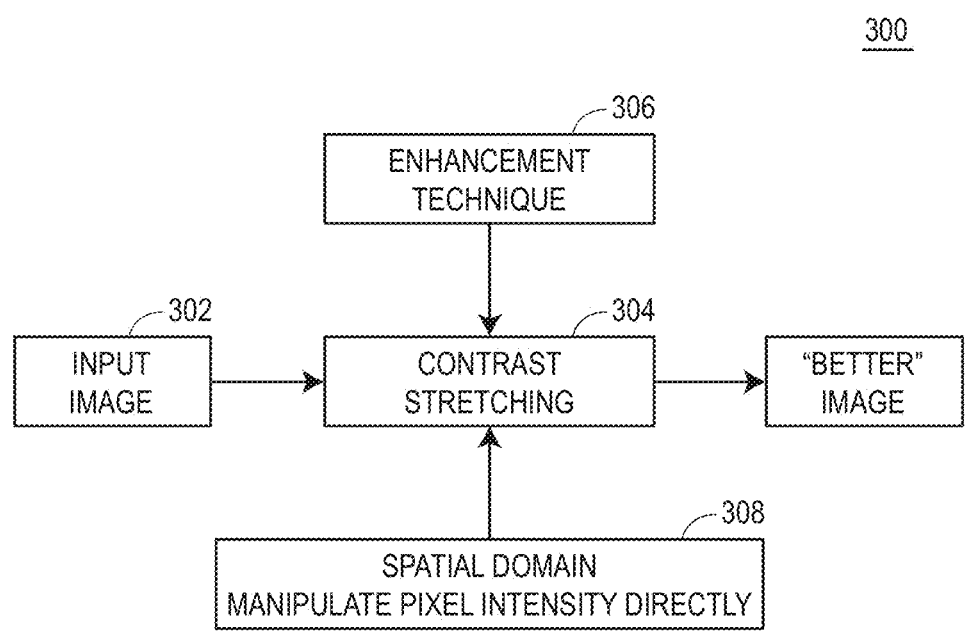
FIG. 3 is a flow diagram of a brightness contrast stretching process that may be implemented as part of the segmentation process of FIG. 2, in accordance with an example.

The techniques for image enhancement are classified to two types: the techniques in spatial domain and the techniques in frequency domain. The first type focuses on manipulating pixel intensity directly. Brightness contrast stretching may be conducted using s=T(r), where r is the grey level of the pixel (x, y) before image enhancement; s is the grey level of the pixel (x, y) after image enhancement. FIG. 3 shows an example brightness contrast stretching process 300 that may be implemented, as an example imagine enhancement. An input image, e.g., the original CT image or pre-processed image, is received from a block 302 image to an image enhance engine, in this case a contrast stretching engine 304. The engine 304 receives enhancement technique data, such as filtered versions of the image in the digital wavelet transform (DWT) domain, from a block 306 and spatial domain manipulated pixel intensity data from a block 308, from which the engine 304 generates an improved/enhanced input version. The process 300 stores the enhanced input image at block 310. The contrast enhancement is determined using the transformation of s=T(r) to stretch the gray level of the object of interest.

In any event, returning to FIG. 2, the pre-processed image data from block 204 is provided to an edge detection block 208.

Edge Detection

Edge detection is a fundamental tool in computer vision. In medical image processing, it is necessary to identify the boundary between the objects and separate the objects from each other. The edge of the image is the local area whose brightness changes significantly. The identification and extraction of the edge is useful for recognizing and understanding the entire image. Detected edges are normally the important features for image segmentation.

In the present techniques, once the image enhancement is conducted, a series of edge detection steps may be taken for preliminary bone tissue segmentation. Example edge detection techniques include applying a Canny edge detection technique to detect the edges of bone tissue and morphological operations to remove spurious edges and sub-edges connection and removal.

In an example, the edge detection block 208 may perform the following. First, edge detection (such as a Canny detector) is applied to obtain the preliminary edges. Second, morphological operations were performed to remove spurious edges and to make the bone edges continuous and smooth. Third, start and end pixels of each sub-edge are detected if there still remain a few disconnected edges. If there are less than 3 (where the number "3" was determined empirically) discontinuous pixels between the start and end pixels, a loop is formed to make them continuous. If the number of connected pixels of each sub-edge is less than three, it is considered isolated and those pixels are removed from the image.

Shape Matching

In addition to edge detection and pre-processing, the system 100 may apply shape matching between images, for example using a shape matching technique. Two images may be used for example. The first image may be the detected edge of each analyzed slice and the second image is one of a number of predetermined bone templates. For example, 100 anatomical bone templates may be accessed for shape matching, where these bone templates have been selected from the bone regions from part of the male and females data available from the Visible Human Project dataset, available from the U.S. National Library of Medicine, National Institutes of Health. Templates may be based on male or female image data, whether collected from the foregoing database or other databases, including local and national databases.

Figure 4:
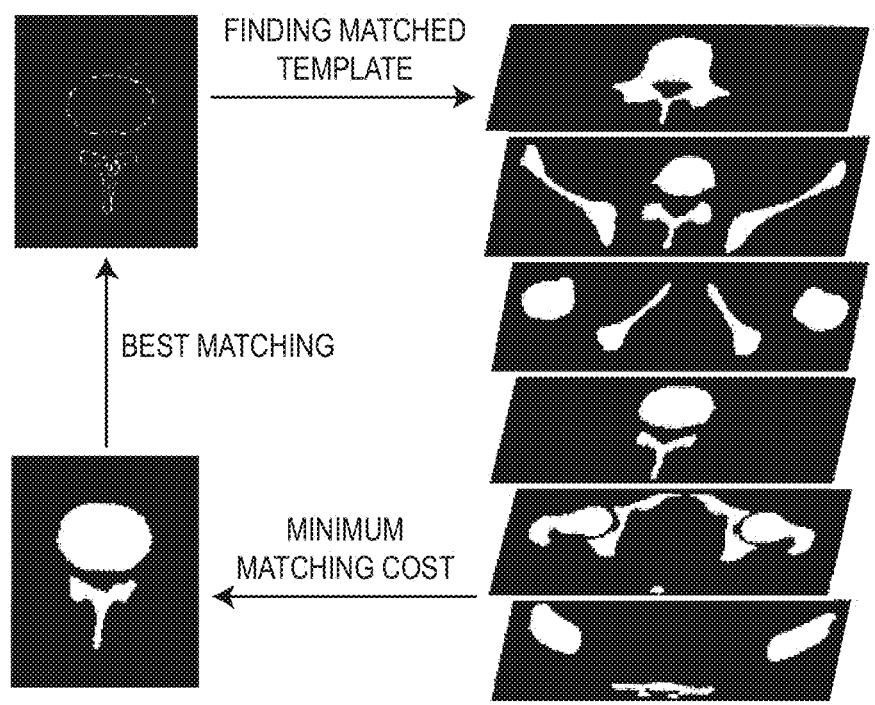
FIG. 4 illustrates a best template matching process, in accordance with an example.

For shape matching, the templates may be compared to similar images of patients in order to determine the best matched template. An overview of an example process 400 is illustrated in FIG. 4. Initially, a number of control points are selected automatically in each image to allow matching between the images. The matching between the objects in the template r and the preliminary segmented bone can be built based on these control points. For example, first, $n_1$ control points on the edges of the objects in the segmented image and $n_2$ control points on the edges of the objects in the template image are sampled, because the edge points represent and describe the shape of object better than other points such as those inside the solid areas. The $n_1$ points on the segmented object and $n_2$ points on the template r object represent a percentage of the total number of points around the edges of the objects in each image.

Second, once the controls points are selected for both the images, the shape context is determined for each point on the contour of the objects in the images. Shape context is a descriptor used for each selected point in the sampled shape as described in the first step. For each point $p_i$ among the $n_1$ and $n_2$ control points on the shape of the corresponding objects in the segmented image and template r, the shape context of the point $p_i$ is defined using a coarse histogram $h_i(k)$ of the relative coordinates of the remaining $n_1-1$ and $n_2-1$ points in the corresponding contours as defined;

$$h_i(k) = \#A\{q \neq p_i | q - p_i \in \text{bin}(k)\}$$

where bin(k) is a region encompassed by two rays and two radii, and for any set A, #A is the number of sample points in the set A. This histogram defines the shape context of the point $p_i$. The histogram bins are uniform in a log-polar space, making the descriptor more sensitive to the positions of nearby sample points.

Third, the matching cost for each individual point is determined. After computing all the shape context descriptors, consider a point $p_i$ in the detected edge, and a point $q_j$ in the template image, the cost of matching a point is as follows:

$$C(p_i, q_i) = \frac{1}{2} \sum_{k=1}^{k} \frac{[h_i(k) - h_j(k)]^2}{h_i(k) + h_j(k)}$$

where $h_i(k)$ and $h_j(k)$ are the K-bin normalized histograms at $p_i$ and $q_j$, respectively. This function determines the matching between any pair of points on the contours of the two objects and allows quantitative assessment of the fitness of any pairing.

Fourth, the matching cost between shapes in the segmented image and the template is determined. The overall cost of a match between the shape in the segmented image and the shape in the template image is the result of minimizing the sum of all individual point cost matches.

This process may be repeated for all the templates (e.g., 100 bone templates). After the best matched template is found, the corresponding training shape models of each best matched template can be directly applied to the preprocessed image for bone segmentation as further described hereinbelow. In this way the shape matching is used to match the detected edge or every one of the available templates to find the best matched template.

Image Registration

As shown in FIG. 2, with the pre-processing 204 and edge detection 208 performed and identifying best matching template, the block 206 may be used for image registration, as now described.

The present techniques employ an RASM structure that that can segment the pelvic bones from CT images automatically and accurately. To facilitate this initialization process is proposed for RASM, using image registration and homogeneity features extracted from pelvic bone.

Image registration is used to get robust training models from different patients despite variations in their bones and/or bone image data (e.g., translation, rotation, scaling, etc.). As applied, in some examples, the image registration of block 206 performs an enhanced homogeneity feature extraction from each training image, correlation coefficient calculation for similarity measure, affine transformation, and Powell algorithm for optimization. Homogeneity, in this project is defined as a composition of two components: standard deviation and discontinuity of the intensities. Standard deviation describes the contrast within a local region in the image and discontinuity measures the abrupt changes of gray level/Hounsfield unit, which is obtained using edge detection.

Suppose $S_{ij}$ is the intensity of a pixel $P_{ij}$ at location (i,j) in an M×N image, and $W_{ij}$ is a size d×d window centered at (i,j).

The standard deviation of pixel $P_{ij}$ is defined as:

$$S_{ij} = \sqrt{\frac{1}{d^2} \sum_{p=i-(d-1)/2}^{i+(d-1)/2} \sum_{q=j-(d-1)/2}^{j+(d-1)/2} (g_{pq} - \mu_{ij})^2}$$

where $0 \le i, p \le M-1$, $0 \le j, q \le N-1$ $\mu_{ij}$ is the mean of the gray levels within window $w_{ij}$, and is defined as:

$$\mu_{ij} = \frac{1}{d^2} \sum_{p=i-(d-1)/2}^{i+(d-1)/2} \sum_{q=j-(d-1)/2}^{j+(d-1)/2} g_{pq}$$

Discontinuity is calculated using Sobel edge detector and it use the magnitude of the gradient as the measure:

$$e_{ij} = \sqrt{G_x^2 + G_y^2}$$

where $G_x$ and $G_y$ are the components of the gradient in x and y direction. Then the two values are normalized and Homogeneity value is determined:

$$S_{ij} = \frac{S_{ij}}{S_{max}};$$

$$S_{max} = \max\{S_{ij}\}$$

$$e_{ij} = \frac{e_{ij}}{e_{max}};$$

$$e_{max} = \max\{e_{ij}\}$$

$$\text{Homo}(i, j) = 1 - E(i, j) \times S(i, j)$$

Since the bone tissues in pelvic CT images have higher intensity values, they appear brighter than other regions in the CT images. From the definition of Homogeneity value defined above, it can be seen that, the greater the intensity differences between a pixel and its neighbor pixels within the window of size d×d, the smaller the value of Homogeneity. This allows the bone tissues to be effectively recognized and extracted for registration.

Figure 5:
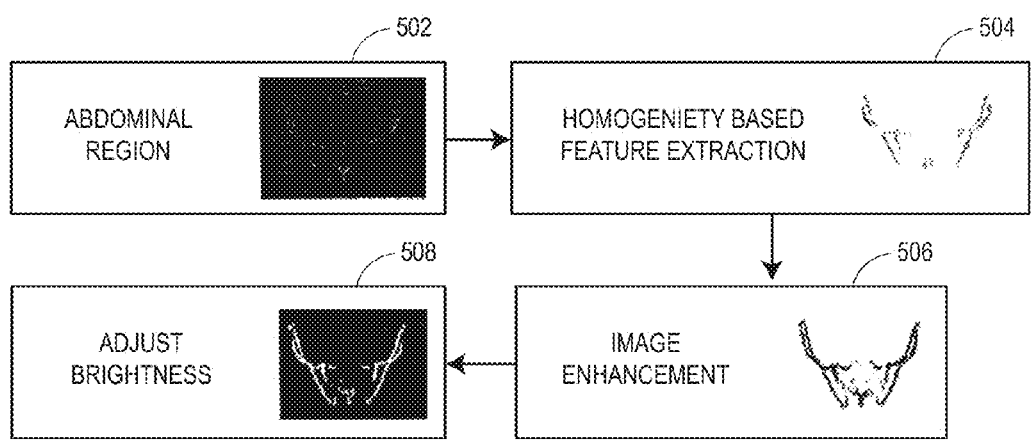
FIG. 5 is a flow diagram of an image registration process, in accordance with an example.
Figure 6:
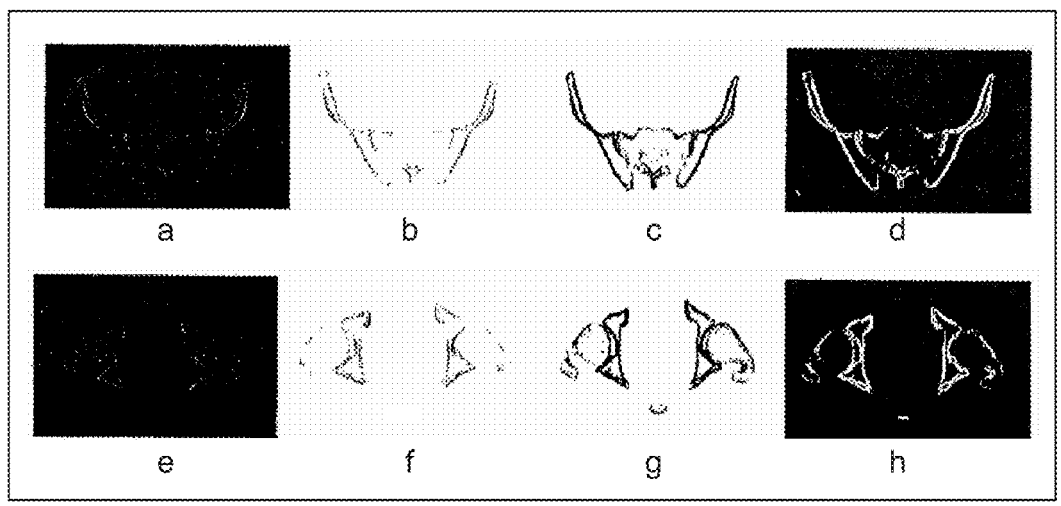
FIGS. 6(a)-6(h) are CT pelvic images showing a homogeneity feature extraction result and brightness enhancement, in accordance with an example.

FIG. 5 shows a flowchart of an example image registration process 500. FIGS. 6(a)-(h) shows the results obtained by Homogeneity extraction from the original images. The results show that the Homogeneity features of bone tissue are clearly detected and the bone shapes are precisely represented. Also, other objects like soft tissues are removed. FIGS. 6(a) and 6(e) are the original pelvic CT images, FIGS. 6(b) and 6(f) are the images based on the Homogeneity feature extraction from FIGS. 6(a) and 6(e), FIGS. 6(c) and 6(g) are brightness enhanced images and brightness is adjusted shown in FIGS. 6(d) and 6(h). The Homogeneity features are utilized for further image registration, which is described in next section.

FIGS. 7(a)-(c) show the results of homogeneity features based image registration. Visually, the size, location and rotation angle of the registered bone is more closely matched with the reference image rather than with the original input image FIG. 7(a). The maximum correlation value of 0.3947 is obtained through registration. FIG. 7(a) is the input image, FIG. 7(b) is reference image, and FIG. 7(c) is the registered image. In this example, the affine parameters are: translation—32, 5.25; rotation—5; scaling—1.028;

In the illustrated example of FIG. 5, the present techniques have been used to receive an original CT image, in which objects that are not part of the target image were removed, and identifying an abdominal region (502) for extraction to produce a feature extracted image (504), which is then image enhanced which may include edge enhancements (506), whereafter brightness adjustment may be performed (508). The resulting image data is provided to the image registration block 206. In this way, FIG. 5 provides an example of homogeneity extraction and adjustment.

Registered Active Shape Model

In general, the standard ASM uses training images labeled with landmark points to generate statistical shape and intensity-level models of a desired object. The shape model can be iteratively deformed to locate the object in a test image. The landmarks are points selected by an expert for the bone region in each registered image during the training phase. Then, the algorithm attempts to fit the shape model to the object. However, the pelvic bones in each original training image have different sizes, rotation angles and locations that may lead to unstable and unreliable shape models for inaccurate bone segmentation.

In order to overcome this limitation, the present techniques use a new process RASM, formed using the image registration technique described above. RASM is developed to create a set of more robust training models which will result in better segmentation. For each level in pelvic CT scans, all the training images are registered to the template to create the registered shape models. The entire RASM algorithm includes two stages: training stage in which registered training models are created, and the testing stage that includes automatic initialization.

FIG. 8 illustrates an example process 600 for implementing RASM. Bone templates are provided from a block 602 to a correlation calculation engine 604. The process 600 seeks to take these bone templates and form registered versions of them, to produce more accurate templates as part of a homogeneity features-based image registration, in which the size, location, scale, and rotation angle of the template is more closely matched with the reference image. In this way, the bone templates are made much more accurate as they adaption is integrated through the entire bone segmentation and fraction detection process.

In the illustrated example, the initial data from the correlation engine 604 is provided to a Powell search optimization determination at 606, where if the correlations are optimized, the registered image is produced at 608, and if not an affine transformation is performed 610 to provide further size, location, scale, and rotation angle manipulation of the bone template image and training image.

In addition to the bone template images from block 602, the process 600 relies upon training images 612. In an example, the bone template images 602 were from the Visible Human Project, while the training images were from hospital patients. 100 bone templates were used and 20 training images. But the number of bone templates and training images, each representing an image at a different CT slice location, may be any number of images from 1-10, 10-100, or 100+. The techniques are not limited by the number of images, although between 10-100 images is generally considered to provide increasingly accurate results.

The training images 612 are provided to a homogeneity feature engine 614 for initial image pre-processing and image enhancement. Initial affine transformations may be applied at a block 616, which provides the adjusted training images to a bilinear interpolation engine 618, which also receives the affine transformation bone template images from block 610. The interpolation engine 618 allows for proper re-sampling of the images. The process then repeats at the correlation engine 604. For registered images 608, the process 600 creates training models 620 that may be used in bone segmentation and fracture detection. These registered images and training models encapsulate the RASM process and the improvements it is capable of offering over conventional ASM techniques. From the training modules 620, an initial position detection 622 may be determined and testing images 624 produced. Thus, the process may be used for bone segmentation and fracture detection of actually obtained CT images.

Initialization for RASM

ASM takes a statistical approach that requires a set of labeled training images to determine variations of the desired shape in testing new images. The standard ASM has been widely used in the recent years, but this method is highly sensitive to initialization. It requires that the initial position be correctly assigned to the training model in order to detect a target object in the image. Then the algorithm can attempt to fit the shape model to the object. If the shape model is not accurately placed, the Standard ASM method often fails to detect the target object.

Figure 9:
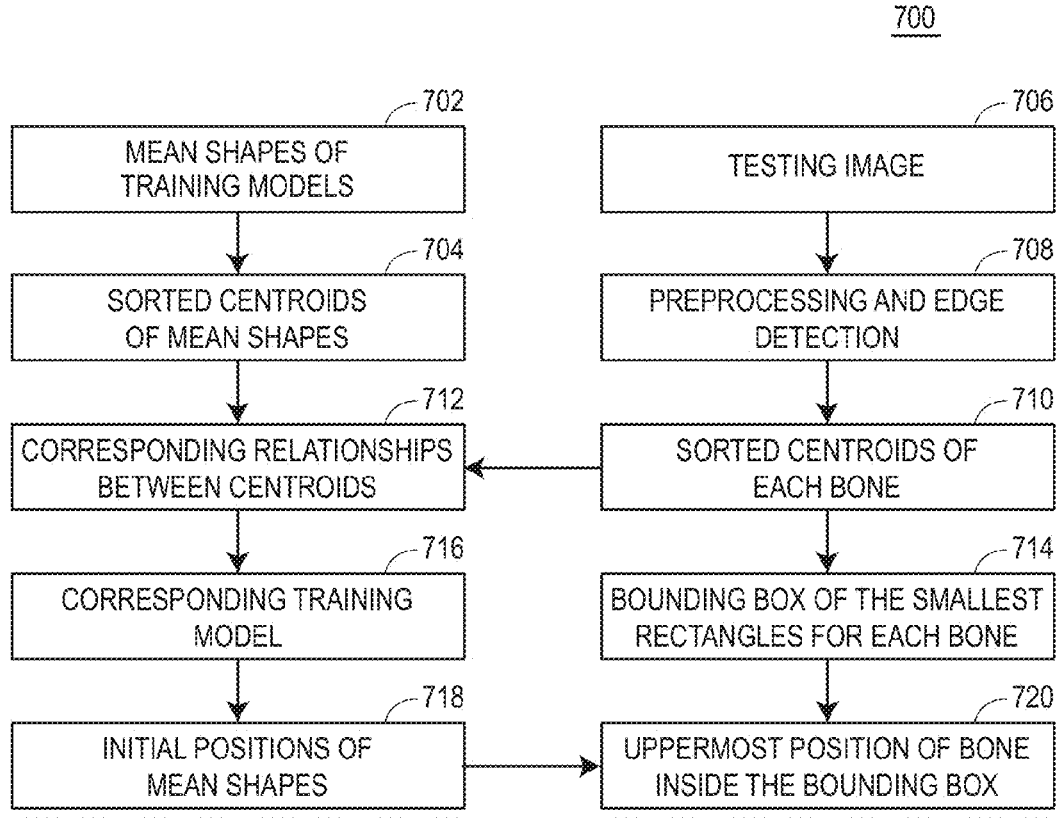
FIG. 9 is a flow diagram of an example initialization process, in accordance with an example.
Figure 10:
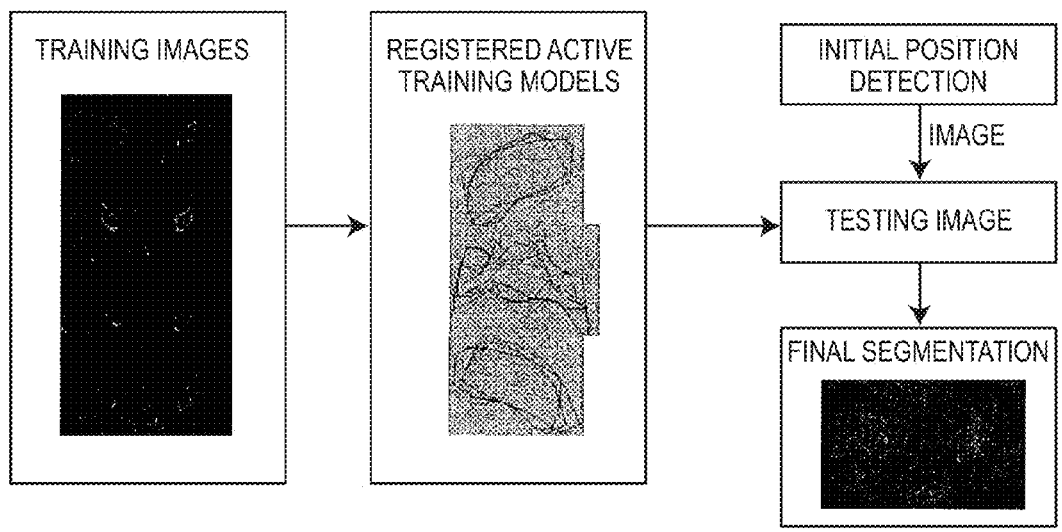
FIG. 10 illustrates segmentation using RASM resulting from the process of FIG. 8 or FIG. 9, in accordance with an example.

The present techniques overcome this shortcoming using a hierarchical initialization process that composes image registration, extracted bone features as well as prior edge detection results to sequentially place the training models for each individual object. This process avoids the need for manually indicating the initial positions. This will avoid human interference and reduce human-caused errors. An example initialization process 700 is illustrated in FIG. 9. The diagram of segmentation using RASM and initialization process is shown in FIG. 10. The algorithm is described as follows.

At a block 702, each training input image, T, is registered to corresponding anatomical template, where n=1, . . . , N. N is the total number of training images. The coordinates for the landmarks in each bone structure are represented as $(x_{p,l}, y_{p,l})$, for p=1, 2, . . . , P, l=1, 2, . . . , L, where p is the number of bones, L is the number of landmarks for each bone. The mean shapes or a training model are obtained using RASM at the block 702. The landmarks are the points selected by the expert to outline the boundary of bone region in each registered training image. During the training process for creating shape models, the uppermost position of each bone is taken as the starting landmark of the shape model.

At a block 704, the centroid $(C_p, D_p)$ is determined for all the mean shapes of the bones from block 706. All $C_p$ values are sorted from the smallest to the largest.

At a block 706, the test image, $E_m$, from block 608 is registered to the corresponding template using homogeneity based image registration, where m=1, . . . , M, and M is the number of test images.

At a block 708, pre-processing and edge detection methods are applied to the test image $E_m$ to obtain the bone edges. The approximated contour of each piece of pelvic bone is detected.

At a block 710, a centroid $(C_p', D_p')$ is determined for all approximated contours of each piece of pelvic bone in test images. All $C_p'$ values are sorted from the smallest to the largest.

At a block 712, the corresponding relationship between these two groups of centroids $(C_p, D_p)$ and $(C_p', D_p')$ is achieved based on their sorted positions, through which the corresponding relationship between different training models and bones in test images is also achieved.

At a block 714, a bounding box of each bone is determined for the test images.

At a block 716, in the test images, within each box bounding, the corresponding training model (716) is assigned the initial position of the means shapes (718) from which the uppermost position of the bone edge (720), then each shape model is correctly placed. FIG. 10 illustrates the process at a high level.

3D Pelvic Bone Visualization

The radiologists usually observe and analyze the patients' data with the combination of both 2D images and 3D models to make accurate diagnostic decisions in clinical diagnosis. In some present examples, we apply the isosurface method to form the 3D pelvic bone models utilizing the segmented pelvic bones from 2D CT slices. In medical imaging area, isosurfaces may be used to demonstrate regions of a specific density in a three-dimensional CT scan. This technique allows the visualization of organs, bones, or other structures. An isosurface is a 3D surface that represents points of an equal constant value within a volume of space-3D data distribution. Isosurface from the volume data is computed using the isosurface parameter specified. Isosurfaces are often used as data visualization methods, can be drawn on the screen very quickly.

After the 2D bone structures are extracted from continuous CT images slices, we set a sphere in 3D domain as $\{x^2+y^2+z^2=R^2\}$ a threshold as 0.5. The pixel value of all the non-bone regions and the bone regions are set to 1. An isosurface is therefore formed based on the threshold value to separate the bone region in each layer from the background. The isosurface connects the points that have the equal pixel value and represent a 3D model of pelvic bone structure.

Fracture Detection and Displacement Measurement

Automated fracture detection is valuable for making fast and accurate decisions and treatment planning. In order to detect the pelvic bone fractures successfully, utilizing the bone information contained in pelvic CT images is very useful. After bone segmentation, a multi-stage process is used for fracture detection in the pelvic CT scans. In some example implementations of the technique, fracture detection of pelvic bones may be implemented in several steps. First, pelvic bone segmentation is conducted via the proposed RASM process. The image is separated into two regions, along an approximated axis of symmetry. The information from these two regions is used to create two sets of multiple adaptive windows. Later, 2-D Stationary Wavelet Transform (SWT) is applied to each window to test the contour discontinuities in each window using boundary tracing. If there is a contour discontinuity in a window, then it is considered as a potential bone fracture.

Figure 11:
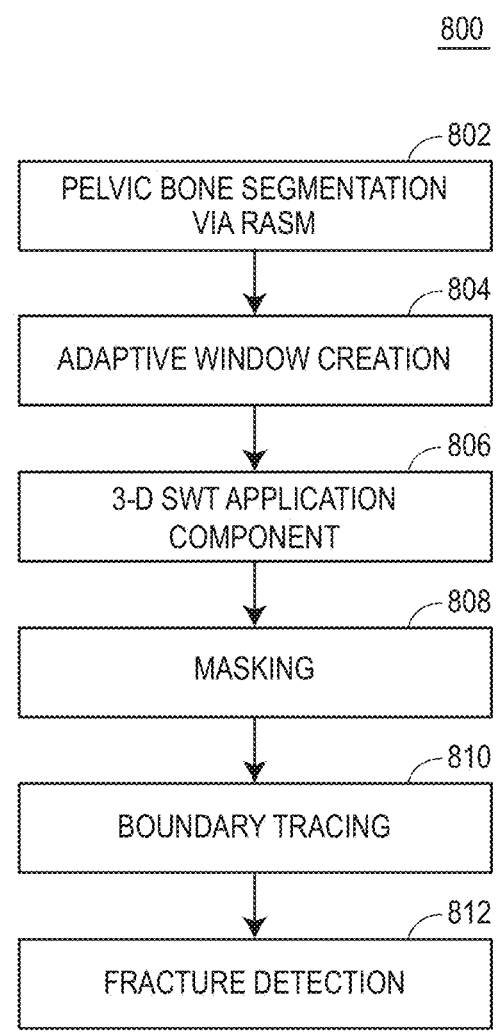
FIG. 11 is a flow diagram of a fracture detection process, in accordance with an example.

FIG. 11 illustrates an example the fracture detection process 800. The process 800 initially includes the pelvic bone segmentation performed using RASM, as discussed herein. Discontinuities around the bone boundary help identify the presence of fracture. Therefore, a detailed view of bone boundary as provided herein facilitates automated fracture detection. Creation of adaptive windows around the bone boundary to facilitate the process of identifying the discontinuities. The adaptive windows may be created across the entire imaging window or selected portions thereof. The present techniques may use adaptive windows created around the bone boundary to obtain a more detailed view of any discontinuities that may indicate fractures around the bone boundary. The appearance of bone fractures in a pelvic CT scan depends on the injury severity. Major fractures are usually visible while minor fractures may not severely distort the edge of the bone; instead they may appear as dual edges or a single sub-edge that is slightly blurred compared to the neighboring edges. Therefore, it is valuable to refine the blurred boundary of each segmented bone in order to achieve accurate fracture detection. The refinement is done using a wavelet transform and edge detection. However, due to local intensity variations, it may be difficult to achieve practical and desirable results by applying wavelet transform to the entire bone structure. Hence, the detected bone boundary may be divided into a series of windows. The size and location of each window is determined by the area of the bone and boundary detected using the RASM. This is called adaptive windowing, herein.

Based on the segmentation formed by the RASM process, landmarks are placed on the boundary of each segmented bone. The process starts from the first segmented pelvic bone region, 802. The adaptive window is created (804) based on each landmark placed on the segmented bone boundary. The size of each window is determined by the distance between each landmark and its previous landmark, as well as the distance between each landmark and its previous landmark. The location of each adaptive window is detected based on the landmarks around the entire bone boundary, i.e., adaptive windowing. The adaptive windows are created as follows.

The coordinates for the landmarks in each bone structure are represented as $(X_{p,1}, Y_{p,1})$, for $p=1, 2, \ldots, N$, $l=1, 2, \ldots, M$, where N is the number of bones, M is the number of landmarks for each bone.

The landmarks are located at the center position of each window. In order to ensure the size of the adaptive windows is suitable to cover the entire bone boundary, the length of the sides of the windows, $S_{p,1}$, is identified using:

$$S_{p,l} = \frac{\sqrt{(x_{p,l-1} - x_{p,l})^2 + (y_{p,l-1} - y_{p,l})^2} + \sqrt{(x_{p,l+1} - x_{p,l})^2 + (y_{p,l+1} - y_{p,l})^2}}{2}$$

where $(x_{p,l-1}, y_{p,l-1})$ is the previous landmark of each landmark $(x_{p,l}, y_{p,l})$ and $(x_{p,l+1}, y_{p,l+1})$ is the next landmark of each landmark $(x_{p,l}, y_{p,l})$.

Since the area of each adaptive window is small, in order to obtain more suitable virtualization effects, each window is scaled to the size of 256×256 by applying a bilinear interpolation technique. After adaptive windowing, 2-D Stationary Wavelet Transform (SWT), non-bone region masking and boundary tracing, as described later, are performed on each window.

The 2-D Stationary Wavelet Transform

After adaptive windowing, 2-D Stationary Wavelet Transform (SWT) 806 is applied on each window in order to refine the blurred boundary of segmented pelvic bone. SWT may be applied as it is designed to overcome any shift variation.

Two sets of coefficients are obtained through wavelet transform, one is approximation coefficients, $cA_j$, and the other is detail coefficients, $cD_j$, where j is the level of decomposition, including horizontal, vertical and diagonal coefficients. Decimation makes wavelet transform a shift-variant process. To overcome this shortcoming, stationary discrete wavelet transform was used.

The scaled window W is first decomposed via the 2-D Stationary Discrete Wavelet Transform. The classical Discrete Wavelet Transform (DWT) is not a space-invariant transform. The SWT is an algorithm which does not decimate the coefficients at every level of decomposition. The filters at level i are up-sampled versions of those at level (i−1). As with the 2-D DWT, decomposition outputs approximation, horizontal, vertical and diagonal coefficients. In this application, three levels of decomposition are applied to window W using the Haar wavelet. The level 3 detail coefficients, $cD_{j+1}(h)$, $cD_{j+1}(v)$, $cD_{j+1}(d)$, are then extracted and used to reconstruct detail arrays $D_h$, $D_v$ and $D_d$ of horizontal, vertical, and diagonal coefficients.

Masking

In this particular example, the next step in the fracture detection is to create a binary version of the chosen detail coefficients from the wavelet transform $W_b$ at a block 808. This binary version not only contains the pelvic bone contour, but also includes other extra and unnecessary edges. A mask is formed to filter these redundant edges out. The mask $W_m$ is formed by converting the smoothed window to a binary image using Otsu's threshold. The threshold is computed to minimize the intra-class variance, defined as a weighted sum of variances of two classes, black and white pixels.

$$\sigma_w^2(t) = w_1(t)\sigma_1^2(t) + w_2(t)\sigma_2^2(t)$$

Weight $w_1$ is probability of each class separated by a threshold t and $\sigma_i^2$ is variance of each class. Minimizing the intra-class variance is the same as maximizing inter-class variance:

$$\sigma_b^2(t) = \sigma^2 - \sigma_w^2(t) = w_1(t)w_2(t)[\mu_1(t) - \mu_2(t)]^2$$

Where $w_i$ is probability of each class and $\mu_i$ is the class mean.

The contour is then extracted from the binary image. The unwanted edges are removed from the binary image to create an edge window. Later, a precise edge window $W_e$ is obtained by removing the extra edges in the image using the pelvic bone contour and the mask. The process is defined as a combination of $W_b$ and $W_m$.

$$W_e = W_b \times W_m$$

Boundary Tracing

After masking, the next step in fracture detection is discontinuities detection, block 810. This is achieved by tracing the extracted bone edges. Sometimes, small artifacts surrounding the extracted bone edges may interfere with the boundary tracing. Therefore, these artifacts must be removed. These are removed by applying morphologic opening to all the objects in the image with area below a specific threshold. The remaining edges are then traced using the 8-neighborhood of each pixel and are returned as a matrix of pixel positions. The traced edges represent the pelvic bone contours. Depending on different types of fracture and severity of fracture, if a fracture is present, as determined by block 812, then multiple boundaries can be identified in the selected window, then it is considered as a potential bone fracture. If the window has a single continuous boundary, then it is considered as no presence of fracture.

Quantitative Displacement Measure

The quantitative displacement measurement is important to determine the pelvic injury severity. For the above detected fracture, the displacement may be determined at block 812 by measuring the distance between the tips of the fractures bone. If $(x_o, y_o)$ is the coordinate of a tip of one piece of the fractured bone and $(x_s, y_s)$ is the coordinate of a tip of the other piece of the same fractured bone, the gap d is calculated as follows:

$$d=\sqrt{(x_o-x_x)^2+(y_o-y_s)^2}$$

Due to the window scaling effect of the previous step, the gap $d_a$ is calculated using $$d_a = \sqrt{(x_o - x_x)^2 + (y_o - y_s)^2} \times \frac{S_{p,t}}{256}$$

Figure 12:
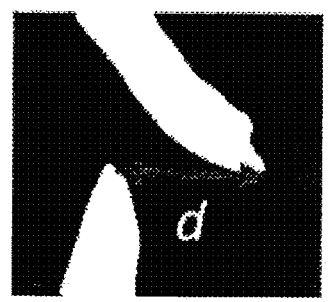
FIG. 12 is a CT image window showing a displacement measurement resulting from a fracture detection process, in accordance with an example.

FIG. 12 shows the displacement measurement in the fractured bone. In any event, the block 812 automatically identifies the fracture and in some examples the severity of the fracture.

Evaluation Measures

In order to quantify the segmentation accuracy, suitable measure is required to evaluate the segmentation results. In this section we give precise definitions for evaluation criteria that we believe are useful and intuitive for evaluation purposes.

Mean Distance: Given two surfaces $S_1$ and $S_2$ we define the distance $d(p_n, S_2)$ between a point $p_n$ on a surface $S_1$ and the surface $S_2$ as:

$$d(p_n, S_2) = \min_{p_m \in S_2} \|p_n - p_m\|_2$$

We define the mean distance between surface $S_l$ and the surface $S_2$ as:

$$d(\text{mean}) = \frac{\sum_{n=1}^{L} d(p_n, S_2)}{L}$$

where $\|\cdot\|_2$ denotes the Euclidean norm, $p_n$ denotes each landmark on surface $S_1$ and $p_m$ denotes each landmark on surface $S_2$, L denotes the total number of landmarks on the surface.

Mis-segmented Area: The idea is to have a measure that represents the uncommon area of the segmented surface and gold standard surface of pelvic bone. Given two surfaces S1 and S2, we define the areas as A1 and A2, the Mis-segmented Area MA of two surfaces S1 and S2 can be defined as:

$$\frac{|G|}{|A_1|} * 100$$

where:

$$G = \{\text{pixels: } p \mid p \in A_l \cup A_2, p \notin A_l \cap A_2\}$$

These results were evaluated by expert radiologists as ground truth for assessment. Visual inspection was also used for assisting to evaluate performance of pelvic bone segmentation. The segmented bones was classified into three categories: Good, Acceptable, and Unacceptable. These categories were determined via consultation with a trauma physician, who identified actual bone contour as the ground truth.

The segmentation results can be represented with a mean distance error, used to identify the segmentation result as one of these three classes. The shapes represented with mean distance errors of less than 1.6±0.2 mm are classified as good, the shapes represented with mean distance errors between 1.6±0.2 mm and 2.2±0.2 mm are classified as acceptable, the shapes represented with mean distance errors more than 2.2±0.2 mm are classified as unacceptable. The segmentation result can also be represented with a mis-segmented area, identifying the segmentation result as one of these three classes. The shapes represented with mis-segmented areas of less than 10% are classified as good, the shapes represented with mis-segmented areas between 10% and 20% are classified as acceptable, the shapes represented with mis-segmented areas more than 20% are classified as unacceptable. Among all the segmentation results of 886 testing images across fifteen patients, 83.07% of them are classified as good, and 13.54% of them are acceptable and 3.39% of them are detected to be unacceptable. The total segmentation accuracy for both good and acceptable classes is 96.61%.

Figure 13:
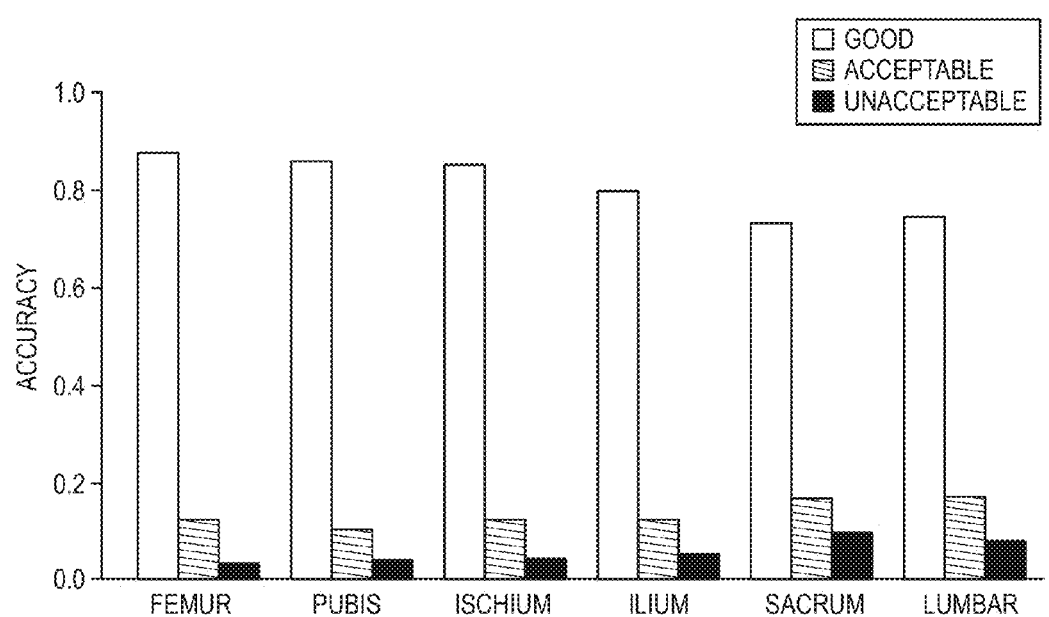
FIG. 13 is a plot of segmentation accuracy results, in accordance with an example.
Figure 14:
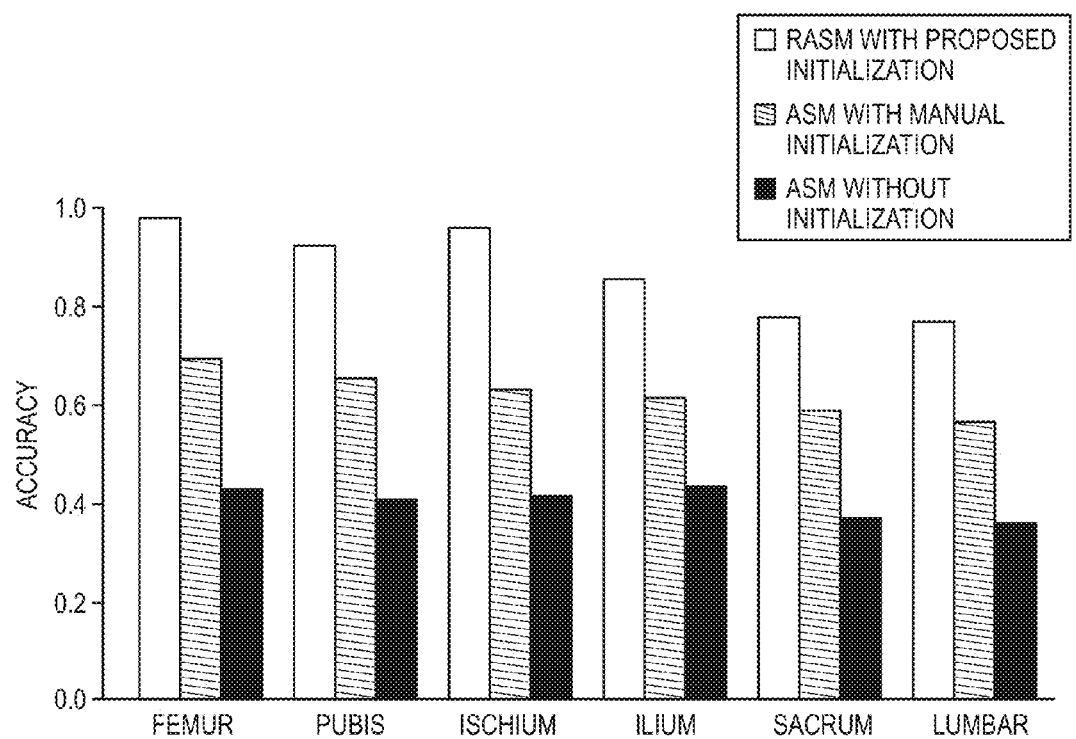
FIG. 14 is another plot of segmentation accuracy results, in accordance with an example.

For different pelvic bone structures, the segmentation accuracy results are shown in FIG. 13. The ilium, ischium, pubis and femur are almost always detected to be at least acceptable; however, the sacrum and lumbar show a number of unacceptable results. This may be because of the variation in bone shapes, blurred edge of the bones, poor quality of the original image, etc. The unacceptable results may be improved by further training of models across a wider dataset or using more landmarks for training the model. Segmentation accuracy, including both good and acceptable results of different pelvic bones using the proposed method, the Standard ASM with manual initialization and the Standard ASM without initialization, are shown in FIG. 14. The results show the superiority of the proposed method on all types of pelvic bones.

Since ASM is a supervised learning method, we are required to test the reliability of the performance of training models. A cross-validation based method is designed to test how much different training data can affect the segmentation results.

For the entire dataset (twenty patients), we shuffle the order of these data sets. Then four folders of data are created based on twenty subjects, each folder has five subjects, and we define the folders as A, B, C and D. Leave one folder out is utilized for the cross-validation process. One subject is selected each time from one folder for testing, the remaining subjects in other three folders are used for creating three different training models, which apply to each selected testing subject. This process is designed to avoid choosing overlapping data for creating different training models and make them independent with each other. Different key pelvic bone structures, including right ilium, left ilium, right femur, left femur, right pubis and left pubis are segmented to demonstrate and compare the performance of training models.

Table 6.2 shows the average segmentation performance for the testing subjects in A using three training models created from B, C, and D. Table 6.3 presents the average segmentation performance for the testing subjects in B using three training models created from A, C, and D. Table 6.4 shows the average segmentation performance for the testing subjects in C using three training models created from A, B, and D. Table 6.5 presents the average segmentation performance for the testing subjects in D using three training models created from A, B, and C. In the tables, MD denotes Mean Distance between the segmented surface and ground truth surface.

For the segmentation performance, 90% of the total testing subjects are classified as good and there is slight difference among the segmentation results using different training models. Based on the entire performance of three different training models on key pelvic bone structures across testing subjects, we can conclude that the selection of training data to form training models has slight influence to the final segmentation results. Also, each training model performs well on different testing subjects and most of the segmentation results are classified as the Good. The created training models in this technique for pelvic bone segmentation are effective and reliable.

TABLE 6.2

Performance of three training models from B, C, and D for five testing subjects in A.

| Testing Subjects/Training Model | Training Model B | Training Model C | Training Model D |
|---|---|---|---|
| First testing subject in A | Good | Good | Good |
| | MD: 0.6 ± 0.2 mm | MD: 1.0 ± 0.2 mm | MD: 1.5 ± 0.1 mm |
| Second testing subject in A | Good | Good | Good |
| | MD: 1.1 ± 0.2 mm | MD: 1.2 ± 0.3 mm | MD: 1.0 ± 0.2 mm |
| Third testing subject in A | Good | Good | Good |
| | MD: 0.8 ± 0.4 mm | MD: 1.0 ± 0.5 mm | MD: 0.9 ± 0.2 mm |
| Fourth testing subject in A | Acceptable | Good | Good |
| | MD: L7 ± 0.6 mm | MD: 1.5 ± 0.2 mm | MD: 1.3 ± 0.3 mm |
| Fifth testing subject in A | Good | Good | Good |
| | MD: 0.8 ± 0.2 mm | MD: 0.8 ± 0.2 mm | MD: 0.9 ± 0.4 mm |

TABLE 6.3

Performance of three training models from A, C, and D for five testing subjects in B.

| Testing Subjects/Training Model | Training Model A | Training Model C | Training Model D |
|---|---|---|---|
| First testing subject in B | Good | Good | Good |
| | MD: 1.5 ± 0.2 mm | MD: 1.6 ± 0.3 mm | MD: 1.3 ± 0.4 mm |
| Second testing subject in B | Good | Good | Acceptable |
| | MD: 0.6 ± 0.2 mm | MD: 0.7 ± 0.4 mm | MD: 2.2 ± 0.8 mm |
| Third testing subject in B | Good | Good | Good |
| | MD: 1.6 ± 0.3 mm | MD: 0.9 ± 0.2 mm | MD: 1.2 ± 0.2 mm |
| Fourth testing subject in B | Good | Acceptable | Good |
| | MD: 1.6 ± 0.2 mm | MD: 2.1 ± 0.7 mm | MD: 1.0 ± 0.2 mm |
| Fifth testing subject in B | Good | Good | Good |
| | MD: 1.1 ± 0.4 mm | MD: 0.8 ± 0.2 mm | MD: 1.0 ± 0.2 mm |

TABLE 6.4

Performance of three training models from A, B, and D for five testing subjects in C.

| Testing Subjects/Training Model | Training Model A | Training Model B | Training Model D |
|---|---|---|---|
| First testing subject in C | Good | Good | Good |
| | MD: 1.2 ± 0.4 mm | MD: 1.0 ± 0.2 mm | MD: 1.3 ± 0.3 mm |
| Second testing subject in C | Good | Good | Good |
| | MD: 0.8 ± 0.2 mm | MD: 0.6 ± 0.2 mm | MD: 0.6 +0.2 mm |
| Third testing subject in C | Acceptable | Acceptable | Good |
| | MD: 2.2 ± 0.5 mm | MD: 1.9 ± 0.3 mm | MD: 1.6 ± 0.3 mm |
| Fourth testing subject in C | Good | Good | Good |
| | MA: 1.6 ± 0.3 mm | MA: 1.5 ± 0.2 mm | MD: 1.3 ± 0.4 mm |
| Fifth testing subject in C | Good | Good | Good |
| | MD: 0.7 ± 0.2 mm | MD: 0.6 ± 0.2 mm | MD: 1.0 ± 0.1 mm |

TABLE 6.5

Performance of three training models from A, B, and C for five testing subjects in D.

| Testing Subjects/Training Model | Training Model A | Training Model B | Training Model C |
|---|---|---|---|
| First testing subject in D | Good | Good | Good |
| | MD: 1.1 ± 0.4 mm | MD: 1.1 ± 0.2 mm | MD: 1.2 ± 0.3 mm |

TABLE 6.5-continued

Performance of three training models from A, B, and C for five testing subjects in D.

| Testing Subjects/Training Model | Training Model A | Training Model B | Training Model C |
|---|---|---|---|
| Second testing subject in D | Good<br>MD: 1.0 ± 0.2 mm | Good<br>MD: 1.5 ± 0.2 mm | Good<br>MD: 1.4 ± 0.4 mm |
| Third testing subject in D | Good<br>MD: 0.8 ± 0.2 mm | Good<br>MD: 1.3 ± 0.3 mm | Good<br>MD: 0.9 ± 0.4 mm |
| Fourth testing subject in D | Good<br>MD: 1.5 ± 0.4 mm | Good<br>MD: 1.6 ± 0.2 mm | Acceptable<br>MD: 2.1 ± 0.6 mm |
| Fifth testing subject in D | Good<br>MD: 0.6 ± 0.2 mm | Good<br>MD: 0.7 ± 0.3 mm | Good<br>MD: 1.0 ± 0.3 mm |

Example Results for Fracture Detection

The results show that the method can successfully detect fracture even in the case of small fractures. Table 6.2 presents the performance of the method detecting fractures. The proposed method is highly sensitive to the discontinuities present in the bone and is also capable of detecting fractures that are very difficult to identify by visual inspection.

Figure 15:
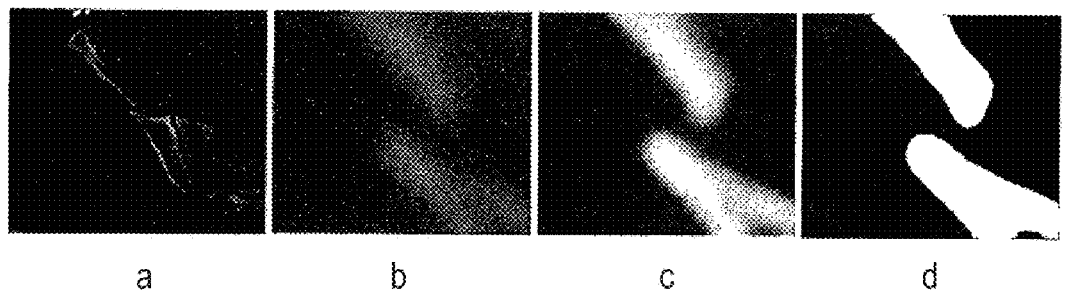
FIG. 15(a)-15(d) are CT image windows showing the results obtained at various stages of a fracture detection process where a fracture has been identified, in accordance with an example.
Figure 16:
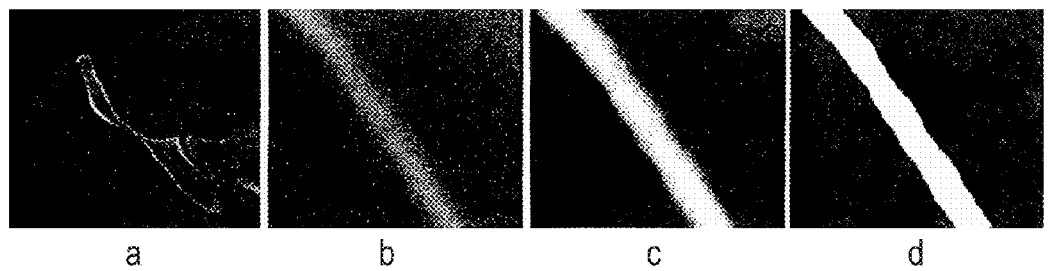
FIG. 16(a)-16(d) are CT image windows showing the results obtained at various stages of a fracture detection process where a fracture has not been identified, in accordance with an example.
Figure 17:
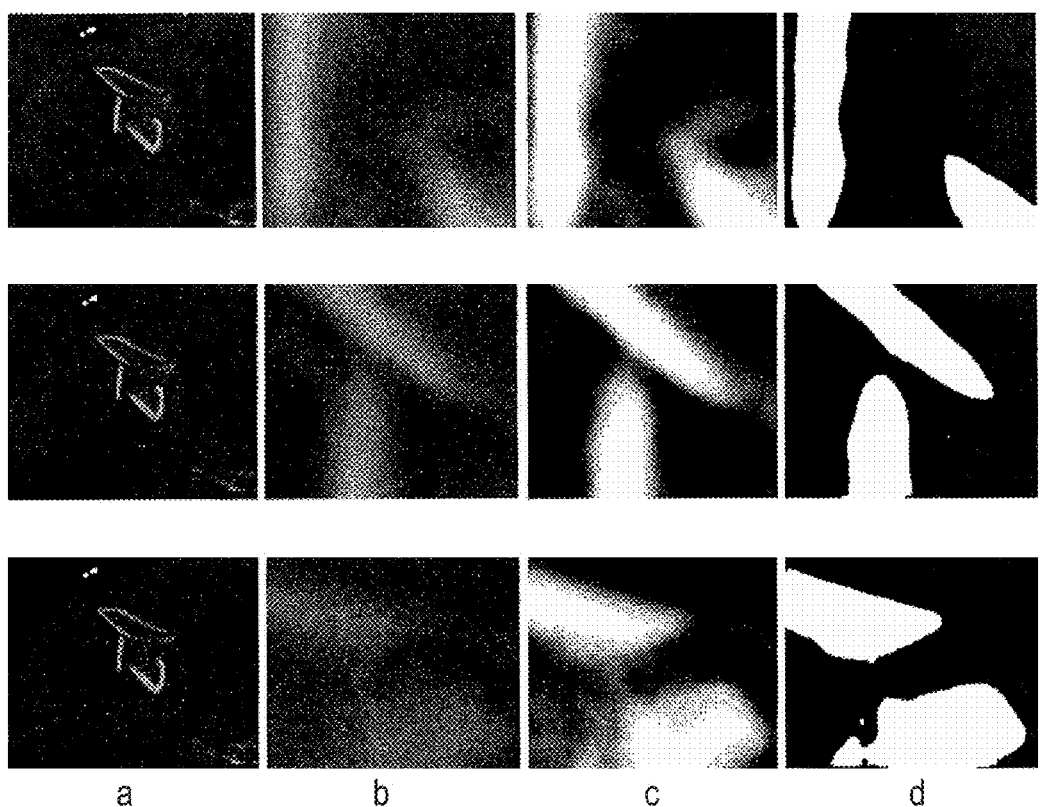
FIG. 17(a)-17(d) are CT image windows showing the results obtained at various stages of a fracture detection process for a patient with a very severe fracture in the right ilium bone, in accordance with an example.

FIG. 15(a)-(d) and FIG. 16(a)-(d) show the results obtained at various stages of fracture detection. In these FIGS. 15 and 16, (a) is the original image, (b) is the extracted adaptive window after being scaled, (c) is the enhanced window after brightness contrast enhancing. This is done for better visualization effect. In addition, FIG. 15(d) shows the final fracture detection results. In FIG. 15, the patient suffers from a minor fracture in right iliac wing. FIG. 15(d) indicates the fracture detected in the right iliac wing. FIG. 16 is the "no fracture" case. The result in FIG. 16 (d) shows that the bone appears smooth with no fracture. FIG. 17(a)-(d) illustrates a patient with a very severe fracture in the right ilium bone. Fractures are detected from the windows of this bone region. Example of detected fractures shown in FIG. 17(d) indicates fractures in three different regions of the right ilium bone. These results are evaluated by an expert radiologist and are considered acceptable. For 7.8% of the cases, the method was unable to capture the fracture. This may be due to the blurred edge of the bones, and the poor quality of the original image.

Table 6.6 presents the performance of the method detecting fractures, in accordance with an example. Relative high accuracy, sensitivity and specificity have been achieved, which show the validity and superiority of the proposed method for fracture detection.

TABLE 6.6

Performance of pelvic bone fracture detection.

| Statistical Results | Accuracy | Sensitivity | Specificity |
|---|---|---|---|
| Rate % | 89.5 | 91.5 | 89.5 |

In order to avoid the existing unbalance of the data, between non-fracture windows (e.g., 53000+ and no fracture windows approx 700, in this example) we randomly select 700 non-fracture windows to make the entire dataset balanced and evaluate the performance of the proposed method. The results are presented in Table 6.7.

TABLE 6.7

Performance of pelvic bone fracture detection.

| Statistical Results | Accuracy | Sensitivity | Specificity |
|---|---|---|---|
| Rate % | 89.2 | 91.5 | 87 |

Example Results of 3D Pelvic Bone Structure Modeling

Figure 18:
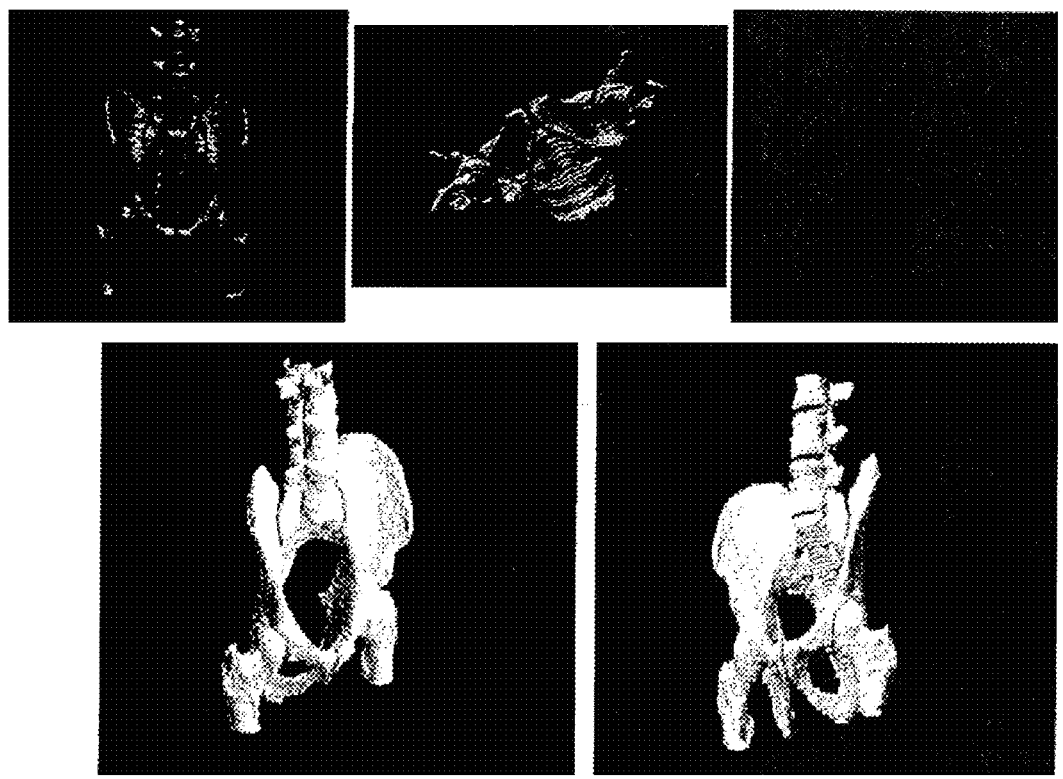
FIG. 18 is a representation of a 3D pelvic bone structure modeling, in accordance with an example.

Since 2D pelvic CT images provide limited and local information in each slice, 3D pelvic bone models are very often required to present a full range of the entire bone structure in clinical diagnosis. The radiologists usually observe and analyze the patients' data of both 2D slices and 3D bone models to make accurate diagnostic decisions. FIG. 18 shows example results of 3D pelvic bone structure modeling. After the pelvic bone from each continuous 2D pelvic CT image is successfully segmented, the 3D model is reconstructed utilizing these extracted 2D bone structures. The models are created using the isosurface method. As we can see, a human's 3D pelvic bone is clearly presented from different points of view. With the present techniques, the pelvic model can be rotated to any angle which will help the physician comprehensively observe the entire pelvic bone structure and detect any abnormality of the patient. In addition, 3D visualization may be used for further validating the 2D segmentation results. However, for the specific measure of fracture or hemorrhage severity, 2D images will likely provide more details.

As discussed above, the techniques herein, implemented in different ways, can provide numerous advantages over conventional techniques. By way of example, and not limitation, these include:

1) A segmentation technique for multiple pelvic CT scans. The technique including pre-processing, shape matching, and Registered Active Shape Model (RASM). For pre-processing, a hierarchical method to perform preliminary bone segmentation may be used that incorporates morphological operations, image enhancement, and edge detection. The proposed hierarchical segmentation method provides automation partially due to the use of a shape matching algorithm.

2) An image registration technique that couples with Active Shape Model to create shape models. The registration method may apply enhanced homogeneity feature extraction, correlation coefficient calculation for similarity measure, affine transformation, and Powell algorithm application.

3) The RASM process proposed herein provides a more robust training model over conventional techniques. The pelvic bones in each original training image have different sizes, rotation angles and locations. Therefore, after the pelvic bones in each training image are registered to the corresponding anatomical template, more robust and reliable training models are created for better segmentation performance.

4) The RASM process provides a hierarchical initialization process that avoids the initialization sensitivity of standard ASM techniques. If the shape model is not accurately placed, the standard ASM techniques may fail to detect the target object, whereas present initialization processes, composed of image registration, extract bone features as well as prior edge detection results to sequentially and automatically place the training models on each individual object.

5) A training model validation process is designed to demonstrate that the selection of training data has a very small effect on the segmentation outcome. The validation process also shows that generated training models are reliable and effective.

6) The techniques provide an automated way to detect fractures in the pelvic bone by analyzing the segmented images and detecting discontinuity. For example, this may be achieved by creating a series of adaptive windows based on the boundaries extracted from the segmentation process performed using RASM. The technique sequentially tests the bone boundary of each slice for contour discontinuities which may indicate fracture.

7) More broadly, as it will be understood upon reading this disclosure, the techniques described herein can be applied for segmentation as well as detection of bone fracture in other types of medical images captured from other parts of human body. The method can also be used for segmentation of unanimated objects.

Figure 19:
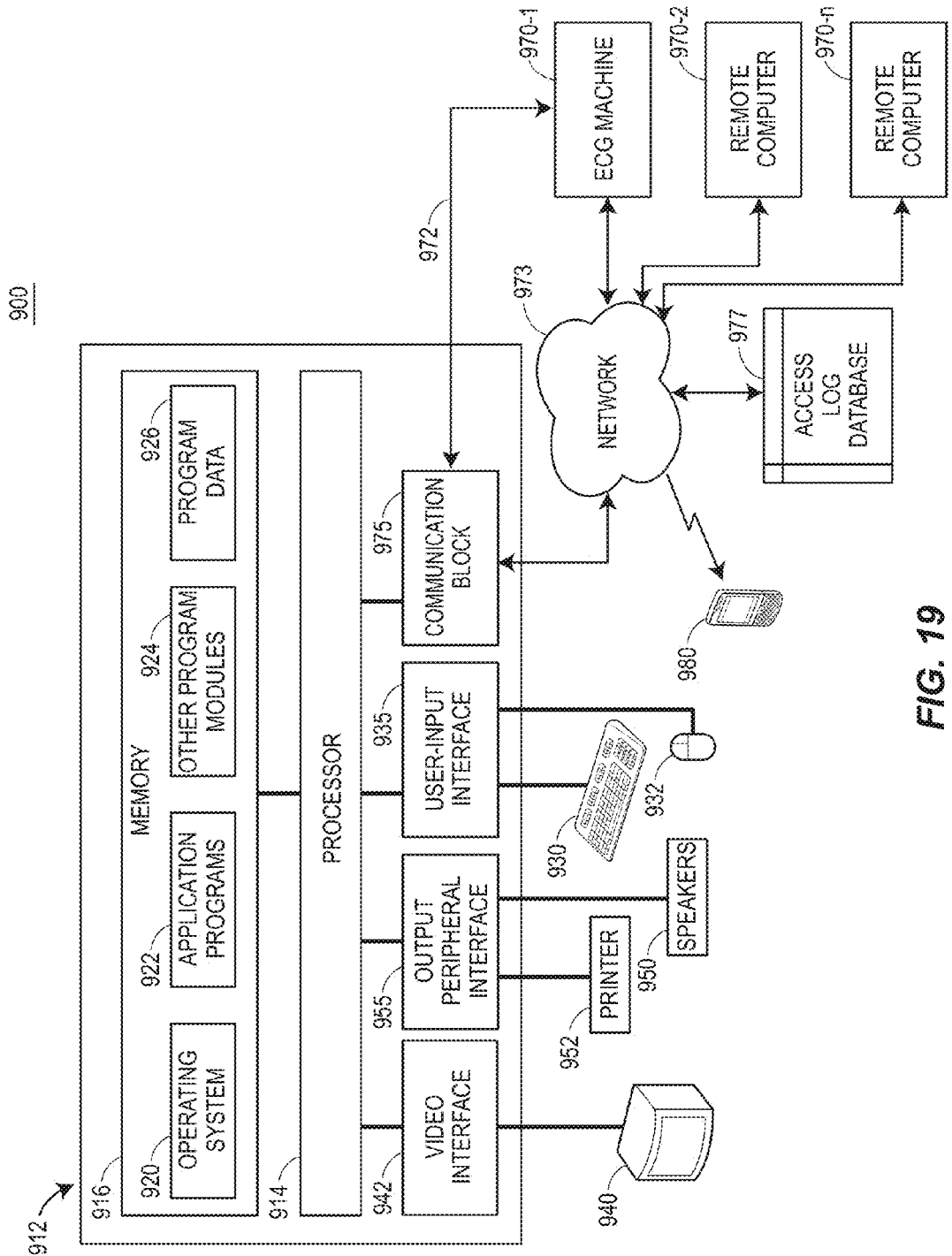
FIG. 19 is a decision support system for performing the processes described herein, in accordance with an example.

With reference to FIG. 19, an exemplary system 900 for implementing the blocks of the method and apparatus includes a general-purpose computing device in the form of a computer 912. The computer 912 may be decision support system for segmenting bone and identifying fractures in pelvic or other bone structures. Components of computer 912 may include, but are not limited to, a processing unit 914 and a system memory 916. The computer 912 may operate in a networked environment using logical connections to one or more remote computers, such as remote computers 970-1, 970-2, . . . 970-n, via a first communication network 972, such as local area network (LAN), and/or a second communication network 973, such as wide area network (WAN) 973, via a communication interface 975. The communication interface 975 may include a variety of hardware for wireless and/or wired communications capabilities. Exemplary wireless communication hardware in the communication interface 975 may include cellular telephony circuitry, GPS receiver circuitry, Bluetooth circuitry, Radio Frequency Identification (RFID) or Near Field Communication (NFC) circuitry, and/or Wi-Fi circuitry (i.e., circuitry complying with an IEEE 802.11 standard), as well as hardware supporting any number of other wireless communications protocols. The communication networks 972 and 973 may be over wireless or wired communication links. Example wired communications may include, for example, USB circuitry, Ethernet circuitry, and/or hardware supporting any number of other wired communications protocols. The network 973 may connect the system 912 to any number of network-enabled devices. The remote computers 970-n may represent a network-enabled wireless terminal, a phone, a tablet computer or personal digital assistant (PDA), a smartphone, a laptop computer, a desktop computer, a tablet computer, hospital terminal or kiosk, a portable media player, an e-reader, or other similar devices (not shown). An example smartphone 980 is shown. Of course, any network-enabled device appropriately configured may interact with the system 900. Such devices may be used to display bone images, for example, via communicating imaging data to a remote device 970-n, 980, etc. having a display for displaying operation of the block 218. Example resulting images are those shown herein.

The remote computers 970 may include other computers like computer 912, but in some examples, these remote computers 970 include one or more of (i) an CT scanning machine, (ii) a medical imaging system, and (iii) a signal records database systems, (iv) a scanner, and/or (v) a signal filtering system In the illustrated example, the computer 912 is connected to a CT scanning machine labeled machine 970-1. The CT scanner 970-1 may be a stand-alone system. In some examples, the computer 912 is integrated with the CT scanner 970-1.

Computer 912 typically includes a variety of computer readable media that may be any available media that may be accessed by computer 912 and includes both volatile and nonvolatile media, removable and non-removable media. The system memory 916 includes computer storage media in the form of volatile and/or nonvolatile memory such as read only memory (ROM) and random access memory (RAM). The ROM may include a basic input/output system (BIOS). RAM typically contains data and/or program modules that include operating system 920, application programs 922, other program modules 924, and program data 926. The memory 916 may store instructions that when executed by the processor 914 perform bone segmentation and fracture detection implementing the processes described herein. The computer 912 may also include other removable/non-removable, volatile/nonvolatile computer storage media such as a hard disk drive, a magnetic disk drive that reads from or writes to a magnetic disk, and an optical disk drive that reads from or writes to an optical disk.

A user may enter commands and information into the computer 912 through input devices such as a keyboard 930 and pointing device 932, commonly referred to as a mouse, trackball or touch pad. Other input devices (not illustrated) may include a microphone, joystick, game pad, satellite dish, scanner, or the like. These and other input devices are often connected to the processing unit 914 through a user input interface 935 that is coupled to a system bus, but may be connected by other interface and bus structures, such as a parallel port, game port or a universal serial bus (USB). A monitor 940 or other type of display device may also be connected to the processor 914 via an interface, such as a video interface 942. In addition to the monitor, computers may also include other peripheral output devices such as speakers 950 and printer 952, which may be connected through an output peripheral interface 955.

Generally, the techniques herein may be coded any computing language for execution on computer 912. CT image data may be obtained from the remote computers 970-1, 970-2, . . . 970-n and stored loaded on to any of the computer storage devices of computer 912. Once the CT image data is obtained, a user may input or select the condition parameters through an input mechanism as described. Although, in other examples, the condition parameters may be pre-selected or automatically determined, for example, based on a particular type of analysis that is to be performed. The output of the executable program may be displayed on a display (e.g., a monitor 940), sent to a printer 952, stored for later use by the computer 912, or offloaded to another system, such as one of the remote computers 970. The output may be in the form of an image, a graph, a table or any combination thereof, by way of example. Operations of the system may be recorded in a log database for future reference as shown. This log database may be accessed at subsequent times. It will be appreciated that the above descriptions are provided by way of example and that numerous modifications may be made within context of the present techniques.

More generally, the various blocks, operations, and techniques described above may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

When implemented in software, the software may be stored in any computer readable memory such as on a magnetic disk, an optical disk, or other storage medium, in a RAM or ROM or flash memory of a computer, processor, hard disk drive, optical disk drive, tape drive, etc. Likewise, the software may be delivered to a user or a system via any known or desired delivery method including, for example, on a computer readable disk or other transportable computer storage mechanism or via communication media. Communication media typically embodies computer readable instructions, data structures, program modules or other data in a modulated data signal such as a carrier wave or other transport mechanism. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared and other wireless media. Thus, the software may be delivered to a user or a system via a communication channel such as a telephone line, a DSL line, a cable television line, a wireless communication channel, the Internet, etc. (which are viewed as being the same as or interchangeable with providing such software via a transportable storage medium).

Moreover, while the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

Thus, although certain apparatus constructed in accordance with the teachings of the invention have been described herein, the scope of coverage of this patent is not limited thereto. On the contrary, this patent covers all embodiments of the teachings of the invention fairly falling within the scope of the appended claims either literally or under the doctrine of equivalents.

What is claimed:

1. A method for analysis of computed tomography (CT) images for diagnosis of bone fractures, the method implemented in a decision support system having a processor and a memory, the method comprising:
    obtaining a CT image of a bone and performing a pre-processing on the obtained CT image to remove a first set of features to create a pre-processed CT image;
    automatically performing an edge detection on the pre-processed CT image to form an edge enhanced CT image and comparing the edge enhanced CT image to a set of bone image templates;
    automatically identifying from among the bone image templates a matching bone image template corresponding to the edge enhanced CT image, wherein the bone image template is a best matching template identified using an affine transformation dependent correlation between the set of bone image templates and the edge enhanced CT image, wherein the automatic identifying is performed using an iterative process over one or more consecutive cycles, wherein each cycle of the iterative process includes,
        performing a correlation determination between the edge enhanced CT image and the one or more bone templates,
        determining if an optimization for the correlation determination between the edge enhanced CT image and the one or more bone image templates satisfies an optimality condition for at least one of the one or more bone image templates, and if the optimality condition is not met, then (i) performing the affine transformation on the edge enhanced CT image and/or on the one or more of the bone image templates, (ii) performing an interpolation on the affine transformed edge enhanced CT image and/or on the affine transformed one or more bone image templates, and (iii) performing another correlation determination until the optimality condition is met and the matching bone image template is identified;
    automatically performing segmentation on the edge enhanced CT image using the matching bone template using an Active Shape Model (ASM) technique, wherein the edge enhanced CT image and the matching bone template are registered to one another forming a registered ASM technique; and
    detecting a fracture in the edge enhanced CT image in response to application of the registered ASM technique.

2. The method of claim 1, wherein each of the set of bone image templates are CT images taken at different slices of a bone.

3. The method of claim 1, wherein the interpolation is a bilinear interpolation and wherein the optimality condition is a Powell optimality condition.

4. The method of claim 1, further comprising performing in a minimization optimization to determine if the optimization is complete.

5. The method of claim 1, further comprising performing contrast stretching on the obtained CT image.

6. The method of claim 1, further comprising adjusting pixel intensities on the obtained CT image.

7. The method of claim 1, wherein the pre-processing on the obtained CT image includes performing a homogeneity based feature extraction on the obtained CT image.

8. The method of claim 1, wherein detecting the fracture in the edge enhanced CT image comprises identifying plurality of adaptive windows of segments on the edge enhanced CT image and analyzing each of the adaptive windows for fracture.

9. The method of claim 8, further comprising:
    applying a 2-D Stationary Wavelet Transform (SWT) to each adaptive window to determine contour discontinuities in each adaptive window;
    creating a binary masking of the each adaptive window;
    performing a boundary tracing of each binary mask formed adaptive window; and detecting for fractures from the boundary traced masked adaptive window.

10. An apparatus comprising:
a computer processor; and
a memory storing computer-readable instructions that, when executed by the computer processor, cause the computer processor to,
obtain a CT image of a bone and perform a pre-processing on the obtained CT image to remove a first set of features to create a pre-processed CT image;
perform an edge detection on the pre-processed CT image to form an edge enhanced CT image and compare the edge enhanced CT image to a set of bone image templates;
identify from among the bone image templates a matching bone image template corresponding to the edge enhanced CT image, wherein the bone image template is a best matching template identified using an affine transformation dependent correlation between the set of bone image templates and the edge enhanced CT image, wherein the identifying is performed using an iterative process over one or more consecutive cycles, wherein each cycle of the iterative process includes instructions to,
perform a correlation determination between the edge enhanced CT image and the one or more bone templates,
determine if an optimization for the correlation determination between the edge enhanced CT image and the one or more bone image templates satisfies an optimality condition for at least one of the one or more bone image templates, and if the optimality condition is not met, then (i) perform the affine transformation on the edge enhanced CT image and/or on the one or more of the bone image templates, (ii) perform an interpolation on the affine transformed edge enhanced CT image and/or on the affine transformed one or more bone image templates, and (iii) perform another correlation determination until the optimality condition is met and the matching bone image template is identified;
perform segmentation on the edge enhanced CT image using the matching bone template using an Active Shape Model (ASM) technique, wherein the edge enhanced CT image and the matching bone template are registered to one another forming a registered ASM technique; and
detect a fracture in the edge enhanced CT image in response to application of the registered ASM technique.

11. The apparatus of claim 10, wherein the interpolation is a bilinear interpolation and wherein the optimality condition is a Powell optimality condition.

12. The apparatus of claim 10, wherein each of the set of bone image templates are CT images taken at different slices of a bone.

13. The apparatus of claim 10, wherein the memory stores further computer-readable instructions that, when executed by the computer processor, cause the computer processor to:
perform in a minimization optimization to determine if the optimization is complete.

14. The apparatus of claim 10, wherein the memory stores further computer-readable instructions that, when executed by the computer processor, cause the computer processor to:
perform contrast stretching on the obtained CT image.

15. The apparatus of claim 10, wherein the memory stores further computer-readable instructions that, when executed by the computer processor, cause the computer processor to:
adjust pixel intensities on the obtained CT image.

16. The apparatus of claim 10, wherein the memory stores further computer-readable instructions that, when executed by the computer processor, cause the computer processor to:
perform a homogeneity based feature extraction on the obtained CT image.

17. The apparatus of claim 10, wherein the memory stores further computer-readable instructions that, when executed by the computer processor, cause the computer processor to:
identify a plurality of adaptive windows of segments on the edge enhanced CT image and analyzing each of the adaptive windows for fracture.

18. The apparatus of claim 17, wherein the memory stores further computer-readable instructions that, when executed by the computer processor, cause the computer processor to:
apply a 2-D Stationary Wavelet Transform (SWT) to each adaptive window to determine contour discontinuities in each adaptive window;
create a binary masking of the each adaptive window;
perform a boundary tracing of each binary mask formed adaptive window; and
detect for fractures from the boundary traced masked adaptive window.

19. A method for analysis of computed tomography (CT) images of bone images, the method implemented in a decision support system having a processor and a memory, the method comprising:
a) obtaining a plurality of bone image templates, each bone image template obtained for a different image slicing of a bone region of a body;
b) obtaining one or more training images of the bone region, the one or more training images taken from a different source than the bone template images;
c) correlating the one or more training images to the plurality of bone image templates to identify a matching bone template, wherein the matching bone template is determined from an optimization;
d) if the matching bone template is not identified from the optimization, then performing an affine transformation on the plurality of bone image templates and/or the one or more training images and performing an interpolation on the plurality of bone image templates and/or on the one or more training images and performing c) again;
e) if the matching bone template is identified, then storing a registered image of the matching bone template and/or of the one or more training images.

20. The method of claim 19, further comprising: determining a registered training model to be applied using an Active Shape Model for segmenting a computed tomography (CT) image of the bone region and identify bone fractures in the CT image.

21. An apparatus comprising:
a computer processor; and
a memory storing computer-readable instructions that, when executed by the computer processor, cause the computer processor to,
a) obtain a plurality of bone image templates, each bone image template obtained for a different image slicing of a bone region of a body;
b) obtain one or more training images of the bone region, the one or more training images taken from a different source than the bone template images;

c) correlate the one or more training images to the plurality of bone image templates to identify a matching bone template, wherein the matching bone template is a determined from an optimization;
d) if the matching bone template is not identified from the optimization, then perform an affine transformation on the plurality of bone image templates and/or on the one or more training images and perform an interpolation on the plurality of bone image templates and/or on the one or more training images and perform c) again;
e) if the matching bone template is identified, then store a registered image of the matching bone template and/or of the one or more training images.

22. The apparatus of claim 17, wherein the memory stores further computer-readable instructions that, when executed by the computer processor, cause the computer processor to: determine a registered training model to be applied using an Active Shape Model for segmenting a computed tomography (CT) image of the bone region and identify bone fractures in the CT image.

* * * * *